United States Patent [19]

Ozawa et al.

[11] Patent Number: 5,631,234
[45] Date of Patent: May 20, 1997

[54] METHOD FOR TREATING ISCHEMIA-REPERFUSION TISSUE INJURY

[75] Inventors: Takayuki Ozawa; Satoru Sugiyama, both of Nagoya; Shigehisa Kitahara, Hino; Katsuhiko Fujii, Hachioji, all of Japan

[73] Assignee: Teijin Limited, Osaka, Japan

[21] Appl. No.: 487,634

[22] Filed: Jun. 7, 1995

Related U.S. Application Data

[63] Continuation of Ser. No. 225,914, Apr. 11, 1994, abandoned, which is a continuation of Ser. No. 955,713, filed as PCT/JP92/00475, Apr. 15, 1992 published as WO92/18120, Oct. 29, 1992 abandoned.

[30] Foreign Application Priority Data

Apr. 15, 1991 [JP] Japan ................................. 3-108163

[51] Int. Cl.$^6$ ............................................. A61K 38/00
[52] U.S. Cl. ................................................... 514/19
[58] Field of Search ...................................... 514/19

[56] References Cited

U.S. PATENT DOCUMENTS

4,927,808  5/1990  Kitahara ................................. 514/19

FOREIGN PATENT DOCUMENTS

| 0276317 | 8/1988 | European Pat. Off. . |
| 0318330 | 5/1989 | European Pat. Off. . |
| 0494405 | 7/1992 | European Pat. Off. . |
| 0501641 | 9/1992 | European Pat. Off. . |
| 0501637 | 9/1992 | European Pat. Off. . |
| 63-61302 | 11/1988 | Japan . |
| 6426516 | 1/1989 | Japan . |
| 6419059 | 1/1989 | Japan . |

OTHER PUBLICATIONS

Kobayashi et al., "The Effects of γ–Glutamylcysteine Ethyl Ester, a Prodrug of Glutathione, on Ischemia–Reperfusion–Induced Liver, Injury in Rats," *Transplantation*, vol. 54, No. 3, pp. 414–418, Sep. 1992.
Ikuta et al., "Implication of Oxygen Radicals on Airway Hyperresponsiveness After Ovalbumin Challenge in Guinea Pigs," *American Review of Respiratory Disease*, vol. 145, No. 3, pp. 561–65, Mar. 1992.
Nishinaka et al., "The Cardioprotective Effect of γ–Glutamylcysteine Ethyl Ester During Coronary Reperfusion in Canine Hearts", *British Journal of Pharmacology*, vol. 104, No. 4, pp. 805–810, Dec. 1991.
Ohtsu et al., "Anticataractogenic Property of γ–Glutamylcysteine Ethyl Ester in an Animal Model of Cataract," *Ophthalmic Research*, vol. 23, No. 1, pp. 51–58, Jan. 1991.
Singh et al., "Relation Between Myocardial Glutathione Content and Extent of Ischemia–Reperfusion Injury," *Circulation*, vol. 80, No. 6, pp. 1795–1804, 1989.
Blaustein et al., "Protective Effects of Glutathione on Ventricular Compliance and Coronary Resistance During Ischemia/Reperfusion," *FASEB*, vol. 3, No. 3, p. A627, Mar. 1989.
Stein et al., "Oxygen Free Radicals and Glutathione in Hepatic Ischemia/Reperfusion Injury," *Journal of Surgical Research*, vol. 50, No. 4, pp. 398–402, Apr. 1991.
Marubayashi et al., "Changes in the Levels of Endogenous Coenzyme Q Homologs, α-Tocopherol, and Glutathione in Rat Liver After Hepatic Ischemia and Reperfusion, and the Effect of Pretreatment with Coenzyme $Q_{10}$," *Biochimica et Biophysica Acta*, vol. 797, No. 1, pp. 1–9, Jan. 24, 1984.
Woodward et al., "Effect of Some Free Radical Scavengers on Reperfusion Induced Arrhythmias in the Isolated Rat Heart," *J. Mol. Cell Cardiol.*, vol. 17, No. 5, pp. 485–493, 1985.
Lackson et al., "Effects of Hypoxia (Ischemia) and Re–Oxygenation (Reperfusion) on Lung Glutathione System," *American Review of Respiratory Disease*, vol. 139, No. 4, p. A39, Apr. 1989.
Pschyrembel, 256 ed., 1990, p. 1142 "Nekrose".
Flohe et al., "The Identity of Glutathione Peroxidase from Erythrocytes and Liver (Contraction Factor I) of the Rat", *Journal of Clinical Chemistry and Clinical Biochemistry*, Mar. 1970.
YiMin et al., "Various Diseases Caused by Free Radical," *Contemporary Medicine Journal*, vol. 18, Period 5, pp. 54–62, Extract, Republic of China, May 15, 1989.
*Journal of Neurochemistry*, vol. 34, pp. 477–486, 1980.
*Circulation*, vol. 81, pp. 201–211, 1990.
*Lung*, vol. 169, pp. 123–138, 1991.
*Current Surgery*, Jan./Feb. 1988 Issue.
Marubayashi et al., Biochimica et Biophysica Acta, vol. 797, No. 1, pp. 1–9, 1984.

*Primary Examiner*—Kimberly Jordan
*Attorney, Agent, or Firm*—Sughrue, Mion, Zinn, Macpeak & Seas

[57] ABSTRACT

The present invention provides a preventive or therapeutic agent for tissue injury caused by active oxygens and free radicals, having for its effective component γ-L-glutamyl-L-cysteine ester derivative indicated in the following general formula:

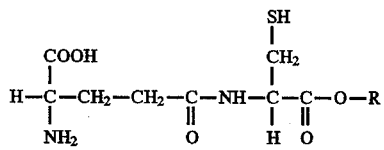

wherein, R is a straight chain, branched or cyclical hydrocarbon group having 1–10 carbon atoms, or a straight chain or branched hydrocarbon group having 1–5 carbons substituted with an aromatic group, or its oxidized dimer.

This compound has the effect of elevating glutathione levels in tissue and biochemically substitute for glutathione thereby performing preventive or therapeutic effects against ischemia-reperfusion tissue injury in the heart, liver and other organs, arrhythmia, as well as lung injury caused by active oxygens and free radicals.

7 Claims, 7 Drawing Sheets

△:P<0.01 VERSUS CONTROL
○:P<0.01 VERSUS OA

METHOD FOR TREATING ISCHEMIA-REPERFUSION TISSUE INJURY

This is a continuation of application Ser. No. 08/225,914 filed Apr. 11, 1994, now abandoned, which is a continuation of application Ser. No. 07/955,713, filed as PCT/JP92/00475, Apr. 15, 1992 published as WO92/18120, Oct. 29, 1992, now abandoned.

TECHNICAL FIELD

The present invention relates to a preventive and therapeutic agent for ischemia-reperfusion tissue injury, a preventive and therapeutic agent for arrhythmia, and a preventive and therapeutic agent for various lung diseases caused by impairment due to active oxygens and free radicals, having for its effective component a γ-L-glutamyl-L-cysteine ester derivative or an oxidized dimer obtained by dehydrogenation of two identical molecules of such.

BACKGROUND ART

Glutathione is present in almost all biological tissues. Glutathione, a major intracellular reducing substance, plays important roles in catalysis, metabolism, transport and in cellular protection. With respect to cellular protection in particular, glutathione displays its action by (1) capturing and detoxifying harmful free radicals and peroxides produced in the body via the SH group of its own molecule, (2) reducing and deactivating active oxygens such as peroxides by means of glutathione peroxidase, and (3) reacting with toxic compounds by means of glutathione S-transferase and excreting those toxic compounds outside the cell in the form of glutathione conjugates, thereby playing roles in antioxidation, detoxification, protection against radiation injury and increasing temperature resistance, etc.

Thus, when the level of tissue glutathione decreases due to various diseases, ageing and so on, the tissue becomes susceptible to injuries. In such cases, it is important to correct the levels of tissue glutathione to normal values in order to restore cell function. In addition, even in cases when tissue glutathione levels are normal, it is thought that increasing tissue glutathione levels can enhance cell protective functions. In actuality, there are reports which state that glutathione and several thiol compounds were effective when used for the purpose of protecting cells from mutagenic substances and carcinogenic substances as well as reducing the size of animal liver tumors caused by such malignant substances.

Moreover, there has been growing attention in recent years focusing on the correlation between depressed levels of glutathione and the overproduction of active oxygens in relation to ischemia and infarction disorders of various tissues including the heart and brain, as well as various types of lung disorders.

In addition, it is gradually becoming clear that when ischemia is canceled by restoration of blood flow, the formation of active oxygens is accelerated, which brings about even more remarkable decrease in glutathione, thereby resulting in the occurrence of more serious disorders. Similar disorders are observed during cessation or restoration of blood flow during transplantation of various organs such as heart, liver, lungs, pancreas and blood vessels. Those disorders also become a problem during incision and removal of organs. Active oxygens and reactive free radicals that are suspected to be the cause of disease are detected both in the cytoplasm of cells that compose tissue and in cellular organelles, especially in mitochondria that produce ATP, which serves as the primary source of energy for cells. It is observed that, in mitochondria, the respiratory chain is the main source of generation of said reactive molecules and the concentration of such has become remarkably elevated during ischemia and reperfusion. In addition, extracellular active oxygens, that are produced on the cell membrane surface of leukocytes that gather at the lesion, are also considered to be harmful to adjacent cells.

The important function of glutathione in the elimination of active oxygens that form during ischemia-reperfusion was first reported in the studies using animals for the disease model (for example, J. Neurochem., Vol. 34, pp. 477–486, 1980; or, Curr. Surgery, January–February edition, pp. 31–33, 1988). Moreover, this was also recognized in human diseases (Circulation, Vol. 81, pp. 201–211, 1990). In each of these cases, the degree of severity of the disease was considered to correlate with the degree of consumption of glutathione.

In addition, it is also reported that in various lung diseases, the severity of the disease state correlates with the decrease in glutathione on the surface of pulmonary epithelial cells (for example, Lung, Vol. 169, pp. 123–138, 1991).

Thus, the significance of replenishing glutathione from outside the body in the prevention and treatment of such diseases would be appreciated, while glutathione itself, the half-life of which in the blood when administered is short, i.e., several minutes, is not very effective in raising tissue glutathione levels. The reason for this is considered that glutathione itself is not efficiently taken up by cells, and glutathione must first be degraded and taken up by cells in the form of peptides and constituent amino acids followed by re-synthesis in the cell.

In an effort to overcome the above-mentioned problems, compounds have been discovered that are superior to glutathione with respect to the ability to elevate tissue glutathione levels. Examples of such compounds include 2-oxothiazolidine-4-carboxylate, γ-L-glutamyl-L-cysteine, and γ-L-glutamyl-L-cysteinyl-glycine ethyl ester (glutathione monoethyl ester). These compounds were discovered through experimentation using human lymphoma cells or animals (for example, Curr. Top. Cell. Regul., Vol. 26, pp. 383–394, 1985; or, Fed. Proc., Vol. 43, pp. 3031–3042, 1984).

The compound represented with general formula (I):

wherein R is an ethyl group, is known according to the description of Japanese Examined Patent Publication No. 63-61302; and the compound wherein R is a straight chain, branched or cyclical hydrocarbon group having 3 to 10 carbon atoms, or a straight chain or branched hydrocarbon group having 1 to 5 carbon atoms substituted with an aromatic group is described in Japanese Unexamined Patent Publications No. 64-19059 and No. 2-258727; and the compound wherein R is a methyl group is known according to the description by Flohé, et al. in Z. Klin. Chem. u. Klin. Biochem., Vol. 8, pp. 149–155 (1970), and is also described in Japanese Unexamined Patent Publication No. 64-26516.

Although the documentation of Flohé, et al. indicates that the γ-L-glutamyl-L-cysteine derivative represented with general formula (I) wherein R is a methyl group serves as a substrate of glutathione peroxidase and is used at 20–30% efficiency compared with glutathione, there are no other descriptions whatsoever that suggest other uses of this compound. In contrast, the previously listed Examined Publication or three Unexamined Publications describe that the γ-L-glutamyl-L-cysteine ester derivative indicated in the above-mentioned general formula (I), or its oxidized dimer, is an ester derivative of a glutathione biosynthesis intermediate and has favorable membrane permeability; and that by means of being efficiently incorporated into tissue and subsequently subjected to deesterification followed by promptly biosynthesetic conversion into glutathione, this compound has the effect of elevating the level of tissue glutathione. These publications also describe that this compound is useful as a therapeutic agent for the treatment of liver disease, cataracts and kidney disease.

In addition, with respect to the possibility that, dependent on animals, tissues and dosages used in experiments, excess γ-L-glutamyl-L-cysteine ester derivative incorporated may be present in tissue as unchanged SH compound, the inventors of the present invention also reported that γ-L-glutamyl-L-cysteine ester derivative has various desirable properties: it serves as a good substrate for glutathione peroxidase, glutathione S-transferase and glutathione reductase in its original form, while, unlike glutathione, it is resistant to breakdown by γ-glutamyl transpeptidase (SEIKAQ, Vol. 61, No. 9 (edition containing the abstract of the 62nd meeting of the Japanese Biochemical Society), p. 800, title no. 1a-Ab08, 1989).

DISCLOSURE OF THE INVENTION

The inventors of the present invention discovered as to the γ-L-glutamyl-L-cysteine ester derivative represented with the above-mentioned general formula (I), and its oxidized dimer that is obtained by dehydrogenation between the two of its identical molecule, which have the ability to elevate tissue glutathione levels as well as biochemically substitute for glutathione, that, in coronary ischemia-reperfusion model using mongrel dogs, these derivatives (1) significantly suppress reduction of glutathione levels in mitochondria of myocardium, (2) significantly suppress reduction of mitochondrial function in myocardium, and (3) significantly suppress the occurrence of arrhythmia during reperfusion resulting in a significant decrease in the mortality rate; and that, in liver ischemia-reperfusion model using rats as well, these derivatives (1) suppress reduction of mitochondrial function during ischemia and promote restoration of such during reperfusion, (2) significantly suppress reduction of glutathione levels in liver tissue, (3) rapidly restore, during reperfusion, liver tissue ATP that had been reduced during ischemia, (4) significantly suppress elevation of lipid peroxide levels in liver tissue following reperfusion, and (5) significantly suppress elevation of the concentration of adenine nucleotides in the hepatic vein immediately after starting reperfusion owing to leakage from liver tissue, as well as elevation of hepatocellular enzyme activity in the blood following reperfusion. The inventors of the present invention also discovered in an asthma model by inhalation of ovalbumin using guinea pigs that these derivatives (1) prevent exacerbation of respiratory tract reactivity (decrease in log[Ach $PC_{200}$]), (2) prevent reduction of the number of β-receptors on the pulmonary membrane and decrease in adenylate cyclase activity, and (3) suppress elevation of xanthine oxidase activity in the lung tissue and bronchoalveolar lavage fluid.

Thus, based on the above-mentioned findings, the present invention relates to the application of γ-L-glutamyl-L-cysteine ester derivative indicated in the following general formula (I):

wherein R is a straight chain, branched or cyclic hydrocarbon group having 1–10 carbon atoms, or a straight chain or branched hydrocarbon group having 1–5 carbons substituted with an aromatic group, or its oxidized dimer obtained by dehydrogenation between the two of its identical molecule, as an effective ingredient, to the prevention and treatment of tissue injury occurring during ischemia-reperfusion of various tissues including heart and liver: more concretely, diseases and tissue injury caused by reduction, cessation or restoration of blood flow: for example, various ischemic diseases such as angina pectoris, myocardial infarction and cerebral infarction; post-operative injury following incision, removal and transplantation of various organs; injury occurring during application of coronary bypass surgery, percutaneous transluminal coronary angioplasty and anticoagulants; and arrhythmia; as well as to the prevention and treatment of various lung diseases including asthma caused by impairment due to active oxygens and free radicals.

MODE OF OPERATION

In the above-mentioned general formula (I), R represents a straight chain, branched or cyclical hydrocarbon group having 1–10 carbon atoms, or a straight chain or branched hydrocarbon group having 1–5 carbon atoms substituted with an aromatic group. In addition, the oxidized dimer refers to a dimer in which disulfide bonds (—S—S—) are formed following dehydrogenation of two identical molecules of the above-mentioned general formula (I).

The γ-L-glutamyl-L-cysteine ester derivative indicated in the above-mentioned general formula (I), or its oxidized dimer, can be manufactured according to the methods described in, for example, Japanese Examined Patent Publication No. 63-61302, Japanese Unexamined Patent Publication No. 64-19059 and Japanese Unexamined Patent Publication No. 64-26516.

In the above-mentioned general formula (I), specific examples of R include a methyl group, ethyl group, n-hexyl group, n-octyl group, isopropyl group, 2-methyl-2-propenyl group, cyclohexyl group and benzyl group. Although the compound indicated in the above-mentioned general formula (I) includes all γ-L-glutamyl-L-cysteine ester derivatives in which a particular R groups is bonded, typical examples of this compound include γ-L-glutamyl-L-cysteine ethyl ester.

In the case of using the γ-L-glutamyl-L-cysteine ester derivative of the above-mentioned general formula (I) or its oxidized dimer as a medical drug pertaining to the present invention, these compounds may be used in their free form or in the form of pharmacologically acceptable acidic or basic addition salts. When used in the form of a salt, the added acidic or basic groups may either be inorganic or organic compounds, and are not limited in any manner as long as they are sufficiently effective when used as a salt, and have no or low toxicity.

The compound of the above-mentioned general formula (I) or its oxidized dimer may be administered orally, non-orally or via the respiratory tract in the desired form by mixing with pharmacologically acceptable carriers, vehicles, solvents, diluents, coloring agents, preservatives, neutralizers and stabilizers for prevention and treatment pertaining to the present invention.

Oral preparations can be either solid preparations such as tablets, granules, powders and capsules, or liquid preparations such as syrups, elixirs, emulsions and suspensions. In addition, non-oral preparations can be in the form of injection preparations, suppositories or external skin preparations. These preparations are made according to routine methods by adding pharmacologically acceptable adjuvants to the compound of the above-mentioned general formula (I) or its oxidized dimer. Moreover, these preparations can also be made into the form of time-released preparations according to known methods.

Solid preparations for oral administration are made into powders by mixing the compound of the above-mentioned general formula (i) or its oxidized dimer with a vehicle such as lactose, starch, cellulose crystal, methyl cellulose, glycerine, sodium alginate, gum arabic, calcium hydrogenphosphate, meta-magnesium aluminum silicate, calcium lactate, sodium chloride, calcium carbonate and kaolin, or, if necessary, made into granules by adding a disintegrating agent such as hydroxypropyl cellulose, polyvinyl pyrrolidone, saccharose, sodium alginate and sodium bicarbonate followed by granulation. Tablets are made by forming these powders and granules into tablets as is, or by adding a glossing agent such as talc or magnesium stearate. Moreover, the above-mentioned granules or tablets can be coated with a base such as methyl methacrylate copolymer or hydroxypropyl methyl cellulose phthalate to form an enteric coated preparation, or coated with ethyl cellulose or a hardened oil to form a time-release preparation. Capsules can be formed into hard capsules by filling with powder or granules, or formed into soft capsules by covering with a gelatin film after suspending or dissolving the compound of the above-mentioned general formula (I) or its oxidized dimer in glycerine, polyethylene glycol or olive oil and so on.

Liquid preparations for oral administration can be formed into a syrup by dissolving the compound of the above-mentioned general formula (I) or its oxidized dimer in water with a sweetener such as glycerine or sorbitol, an elixir by adding ethanol or essence, or an emulsion or suspension by adding polysorbate 80, sodium carboxymethyl cellulose or gum arabic and so on.

Injection preparations are formed into single-dose or long or short-term continuous injection preparations for subcutaneous, intramuscular, intravenous or intraarterial injection by dissolving the compound of the above-mentioned general formula (I) or its oxidized dimer in distilled water for injection together with a pH regulator such as disodium hydrogenphosphate, sodium dihydrogenphosphate, sodium hydroxide, hydrochloric acid, lactic acid or sodium lactate, an isotonic agent such as glucose or sodium chloride, and an SH group stabilizer such as sodium bisulfite, ascorbic acid or sodium ethylene diamine tetraacetate, and filling into ampules or polyethylene or glass containers following aseptic filtration. In addition, injection preparations of the type that are prepared as needed can be made by freeze-drying in a vacuum following the addition of dextrin, cyclodextrin, mannitol, gelatin and so on. In addition, the compound of the above-mentioned general formula (I) or its oxidized dimer may also be formed into an injection preparation contained in liposomes or microspheres in accordance with known methods.

Suppositories can be made by heating and melting the compound of the above-mentioned general formula (I) or its oxidized dimer with polyethylene glycol, lanolin, mono-, di- or triglycerides of fatty acids or cocoa butter, and coating with gelatin, etc., after either cooling to plasticize, or suspending or dissolving in soy bean oil, polyethylene glycol and so on.

External skin preparations can be made by adding the compound of the above-mentioned general formula (I) or its oxidized dimer to polyethylene glycol, white vaseline or liquid paraffin, etc., and may be in the form of an ointment, cream or gel and so on.

Preparations administered via the respiratory tract are administered in the form of fine granules of the compound of the above-mentioned general formula (I) or its oxidized dimer using routine inhalation methods. It is desirable that the fine particles containing the drug as its effective component be in the form of an aerosol or powder, and have a particle size of 0.5–50 μm. Examples of devices that can be used to produce the aerosol include ultrasonic and jet spray type nebulizers, and sprayers using lower alkanes or fluorinated alkanes as the propellant. In addition, powders are administered using a simple inhaler coupled with spontaneous or forced inhalation.

Although there are no particular limitations on the concentration of the compound represented with general formula (I) or its oxidized dimer in the present medical drug preparation, in general, 0.1–70% by weight, and preferably 1–50% by weight, is suitable for the concentration in the preparation. In addition, although there are also no limitations on its dosage, 0.01–5 g/day/patient, and preferably 0.1–2.5 g/day/patient, is suitable. With the exception of continuous injection, the number of administrations is normally 1–4 times per day.

EXAMPLES

Although the following provides a detailed explanation of the present invention using the Examples, the present invention is not limited by said Examples.

Example 1

Preventive and therapeutic effects of γ-L-glutamyl-L-cysteine ethyl ester (γ-GCE) on ischemia-reperfusion injury and accompanying arrhythmia in a coronary ischemia-reperfusion model using dogs.

Experimental Method

After anesthetizing 52 adult mongrel dogs of either sex weighing ca. 10 kg by intraperitoneal administration of 50 mg/kg of sodium pentobarbital, breathing tubes were immediately intubated endotracheally and artificial ventilation was continued using a Harvard ventilator. Electrocardiogram electrodes were attached, and monitoring and recording were continued throughout the experiment. Following insertion of cannulas in the right femoral vein and right femoral artery, the cannulas were used for continuous intravenous drip of physiological saline to replenish water or administration of the test preparation, and monitoring of arterial blood pressure, respectively. After performing left thoracotomy in the fourth or fifth intercostol space, the pericardium was torn to expose the heart. Ischemia was induced by ligating the left anterior descending coronary artery immediately distal to the first diagonal branch, while reperfusion was performed by subsequently removing that ligation.

The animals were divided into four groups. Group 1 (n=9) was subjected to ischemia for 2 hours, group 2 (n=17) was subjected to ischemia for 2 hours followed by reperfusion for 1 hour, group 3 (n=10) was subjected to ischemia for 2 hours followed by reperfusion for 1 hour plus intravenous injection of 10 mg/kg of γ-GCE just before reperfusion, and group 4 (n=16) was subjected to 2 hours of ischemia followed by 1 hour of reperfusion plus intravenous injection of 10 mg/kg of reduced glutathione (GSH, control drug) just before reperfusion.

Evaluation of ischemia-reperfusion injury was performed, following completion of ischemia-reperfusion, by measuring (1) glutathione content of mitochondria, and (2) mitochondrial function, and so on, at the ischemic or reperfused area and the normal area of the heart. Mitochondria was obtained by removing the heart immediately after the end of ischemia or reperfusion, washing with cold physiological saline, promptly cutting out the ischemic or reperfused area and the normal area, and immediately performing preparation from the respective area according to the method described by Hatefi, et al. in Arch. Biochem. Biophys., Vol. 94, pp. 148–155, 1961.

The glutathione content of the mitochondria was measured by applying the method described by Tietze in Anal. Biochem., Vol. 27, pp. 502–522, 1969 to the supernatant obtained by immediately adding 1/10 vol of 27.5% (w/v) sulfosalicylic acid dihydrate aqueous solution to the prepared mitochondria suspension followed by protein denaturation and centrifugation. Evaluation of mitochondrial function was performed according to the method described by Sugiyama, et al. in Am. Heart J., Vol. 100, pp. 829–837, 1980, by polarographically measuring respiratory ability using an oxygen electrode and determining the rate of oxygen consumption is state III (St. III $O_2$) and the respiratory control index (RCI).

Evaluation of arrhythmia was performed by analyzing the electrocardiogram to determine the presence of arrhythmia, or in other words, the number of ventricular premature beats, as well as the total duration of ventricular tachycardia, which was defined as more than three successive ventricular premature beats.

Results

1. Mortality Rate

Table 1 indicates the mortality rates during 2 hours of ischemia followed by 1 hour of reperfusion. In contrast to the mortality rate during reperfusion being 0 in group 3, which was administered with γ-GCE just before reperfusion, in group 2, which was not administered with a drug, and group 4, which was administered with GSH, ca. 50% of the animals died due to ventricular fibrillation during reperfusion. The above results indicate that γ-GCE has excellent preventive and therapeutic effects against sudden death caused by reperfusion injury.

Analyses of ischemia-reperfusion injury as well as arrhythmia described in the following sections 2 and 3 were performed on a total of 32 animals comprised of the surviving 8 animals in each group. Data was expressed in terms of the mean ± standard deviation, and evaluation of significance was performed according to Dunnett's test. Cases in which P was less than 0.05 were considered to be statistically significant.

2. Preventive and Therapeutic Effects on Ischemia-Reperfusion Injury

Table 2 indicates the glutathione contents of cardiac muscle mitochondria at normal area and ischemic or reperfused area. The content of reduced glutathione (GSH) and total glutathione, i.e., reduced form (GSH) plus oxidized form (GSSG), at ischemic or reperfused area, decreased to ca. 80% of the normal area after 2 hours of ischemia as can be seen in group 1, and further decreased to ca. 60% after subsequent 1 hour of reperfusion as can be seen in group 2. In contrast, in group 3, in which 10 mg/kg of γ-GCE was administered just before reperfusion, glutathione levels reined high, i.e., in the order of 85–88%, even after reperfusion. Not only did administration of γ-GCE significantly suppress further reduction of glutathione during the reperfusion, but it also displayed a tendency to recover the glutathione reduction that had occurred during the 2 hours of ischemia. On the other hand, in group 4, which was administered with GSH, no such effects were observed. The above results indicate that γ-GCE has superior properties in membrane permeability and has excellent preventive and therapeutic effects on the reduction of glutathione level of intracellular organelle mitochondria during ischemia-reperfusion.

Figure 1A:
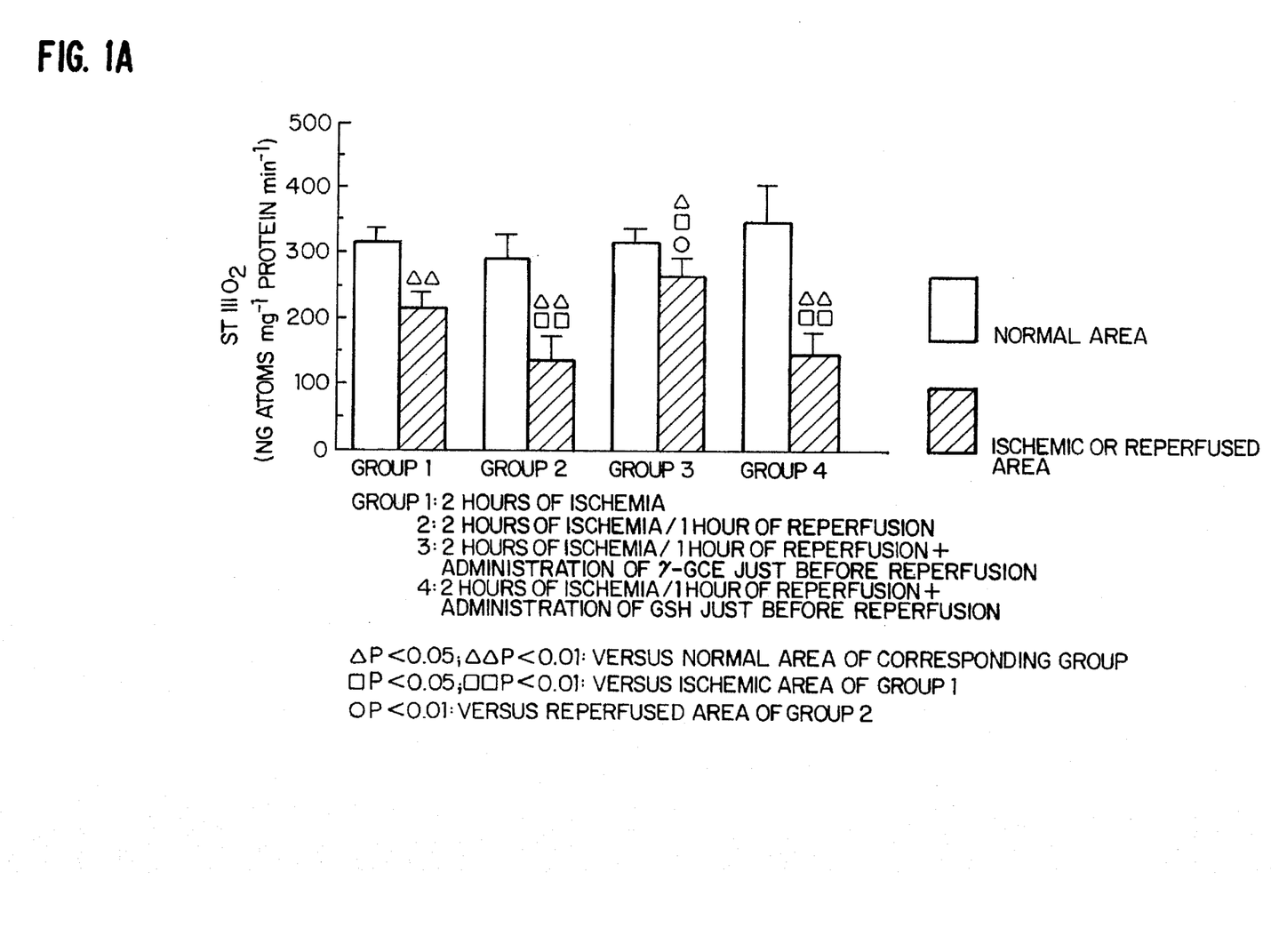
FIG. 1A and FIG. 1B are graphs respectively indicating the preventive and therapeutic effects γ-L-glutamyl-L-cysteine ethyl ester of (γ-GCE) on the cardiac muscle mitochondrial dysfunction, or in other words, the decreased rate of state III oxygen consumption (St. III $O_2$), and the decreased respiratory control index (RCI) in coronary ischemia-reperfusion model using dogs.
Figure 1B:
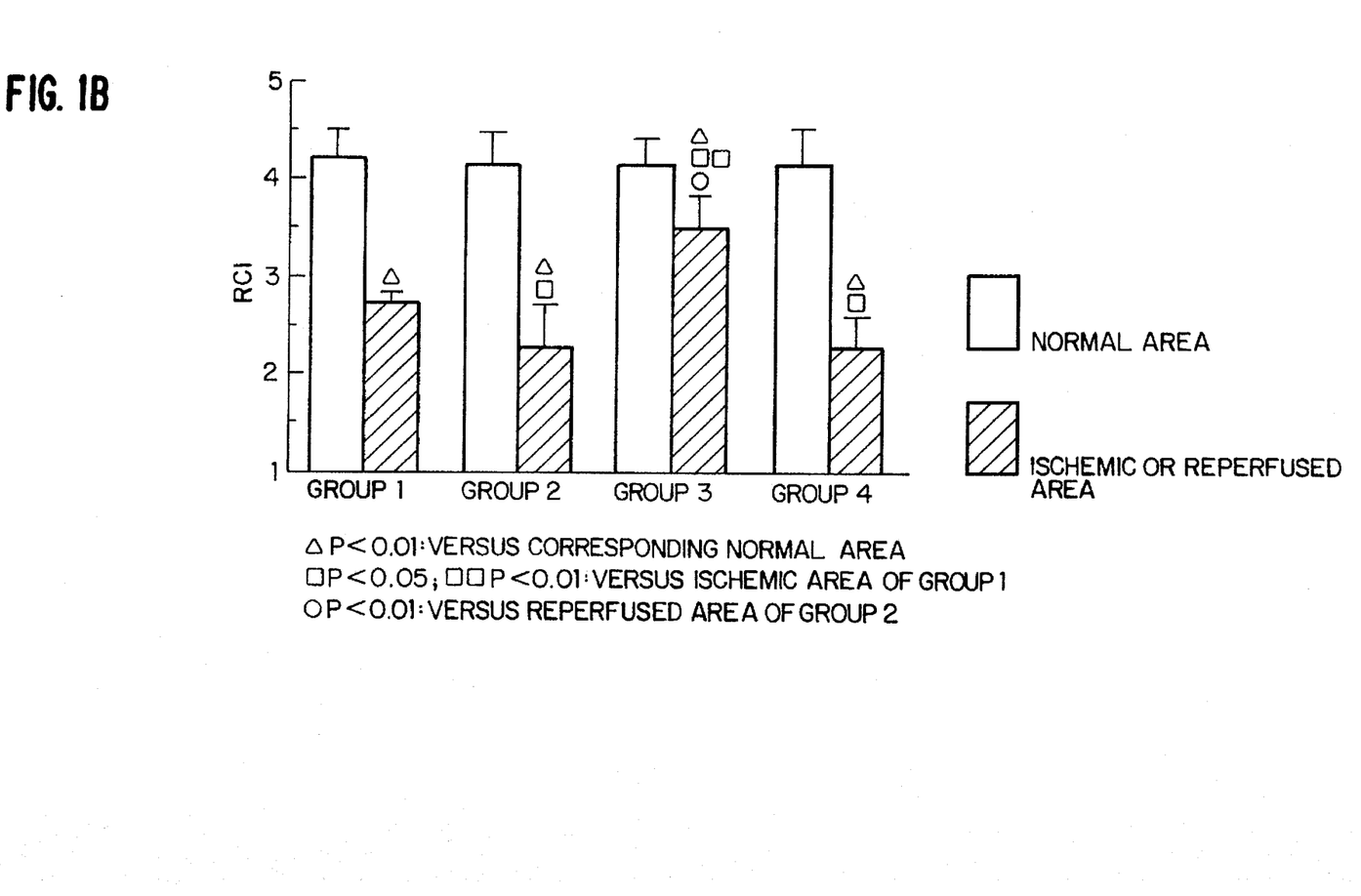

FIG. 1A and FIG. 1B indicate mitochondrial function of cardiac muscle, at both normal area and ischemic or reperfused area, i.e., the rate of oxygen consumption in state III (St. III $O_2$), and the respiratory control index (RCI), respectively. In group 3, in which 10 mg/kg of γ-GCE was administered just before reperfusion, not only was the further reduction in mitochondrial function during reperfusion completely suppressed, but also was the reduced function that had resulted during ischemia before administration of γ-GCE significantly improved. In contrast, in group 4, which was administered with GSH, no protective effects were observed whatsoever. The above results indicate that γ-GCE has superior effects on prevention and treatment of coronary ischemia-reperfusion injury.

3. Preventive and Therapeutic Effects on Arrhythmia

Table 3 indicates the number of arrhythmia (in other words, the ventricular premature beats) and the total duration of ventricular tachycardia, in which more than three successive ventricular premature beats occurred, during ischemia-reperfusion. As can be seen in group 2, which was not administered with a drug, ventricular premature beats occurred almost exclusively during the 60 minutes of reperfusion rather than during the 120 minutes of ischemia. This remarkable occurrence of arrhythmia during reperfusion was strikingly suppressed in group 3, which was administered with 10 mg/kg of γ-GCE just before reperfusion, while, in group 4, which was administered with GSH, said occurrence was not suppressed at all. On the total duration of ventricular tachycardia, likely on the number of ventricular premature beats, γ-GCE remarkably suppressed its increase during reperfusion, while GSH did not show such effect whatsoever. The above results indicate that γ-GCE has superior preventive and therapeutic effects against the occurrence of arrhythmia accompanying coronary ischemia-reperfusion injury.

TABLE 1

Mortality Rate of Dogs During Coronary Ischemia-Reperfusion Experiment (Number of dogs that died/ Number of dogs in experiment)

|  | 2 Hours of Ischemia | 1 Hour of Reperfusion |
|---|---|---|
| Group 1 | 1/9 |  |
| Group 2 | 1/17 | 8/16 |
| Group 3 | 2/10 | 0/8 |
| Group 4 | 1/16 | 7/15 |

Group 1: 2 hours of ischemia
Group 2: 2 hours of ischemia/1 hour of reperfusion
Group 3: 2 hours of ischemia/1 hour of reperfusion + Administration of γ-GCE just before reperfusion
Group 4: 2 hours of ischemia/1 hour of reperfusion + Administration of GSH just before reperfusion

TABLE 2

Glutathione Contents of Mitochondria in Cardiac Muscle Following Coronary Ischemia-Reperfusion in Dogs

|  | Normal Area | Ischemic or Reperfused Area |
|---|---|---|
| GSH + GSSG |  |  |
| Group 1 | 4.03 ± 0.57 | 3.26 ± 0.51* |
| 2 | 4.12 ± 0.40 | 2.93 ± 0.66**† |
| 3 | 4.06 ± 0.52 | 3.57 ± 0.46§ |
| 4 | 3.94 ± 0.33 | 2.44 ± 0.57**†† |
| GSH |  |  |
| Group 1 | 3.59 ± 0.46 | 2.87 ± 0.40* |
| 2 | 3.67 ± 0.45 | 2.16 ± 0.64**† |
| 3 | 3.68 ± 0.54 | 3.12 ± 0.40§ |
| 4 | 3.67 ± 0.37 | 2.17 ± 0.52**† |
| GSSG |  |  |
| Group 1 | 0.44 ± 0.28 | 0.40 ± 0.17 |
| 2 | 0.45 ± 0.14 | 0.37 ± 0.15 |
| 3 | 0.38 ± 0.09 | 0.45 ± 0.15 |
| 4 | 0.27 ± 0.08 | 0.27 ± 0.09 |

Values are expressed as mean ± standard deviation
*$P < 0.05$; **$P < 0.01$ versus normal area of corresponding group
† $P < 0.05$; †† $P < 0.01$ versus ischemic area of Group 1
§ $P < 0.01$ versus reperfused area of Group 2

TABLE 3

Arrhythmia during Coronary Ischemia and Reperfusion in Dogs

|  | Number of Ventricular Premature Beats | | Total Duration of Ventricular Tachycardia (sec) | |
|---|---|---|---|---|
|  | 2 Hours of Ischemia | 1 Hour of Reperfusion | 2 Hours of Ischemia | 1 Hour of Reperfusion |
| Group 1 | 30 ± 31 |  | 3 ± 6 |  |
| Group 2 | 11 ± 15 | 1376 ± 956 | 0 ± 1 | 1029 ± 671 |
| Group 3 | 40 ± 51 | 32 ± 30* | 1 ± 2 | 3 ± 5* |
| Group 4 | 42 ± 43 | 1731 ± 1574 | 1 ± 2 | 983 ± 959 |

Values are expressed as the mean ± standard deviation.
*$P < 0.01$ versus 1 hour of reperfusion of Group 2

Example 2

Preventive and therapeutic effects of γ-GCE on ischemia-reperfusion injury in a liver ischemia-reperfusion model using rats.

Experimental Method

Male Wister rats weighing 250–300 g were fasted with free access to water 24 hours before the experiment. Seventy-two rats were divided into three groups of 24 animals each, i.e., the control group, the GSH administration group and the γ-GCE administration group. Each rat was anesthetized by intraperitoneal administration of 40 mg/0.8 ml/kg of sodium pentobarbital, and the femoral vein was cannulated. In the GSH group and the γ-GCE group, 50 mg/kg of GSH or γ-GCE respectively were administered intravenously. Physiological saline was then infused for volume replacement in each group, as a continuous intravenous infusion at a rate of 0.8 ml/hr with an injection pump throughout the experiment. Thirty minutes after starting injection of physiological saline, the abdomon was opened by a midline incision and the liver hilus was exposed. According to the method described by Hasselgren, et al. in J. Surg. Res., Vol. 34, pp. 409–414, 1984, all vessels to the left and median lobes of the liver, more specifically, hepatic artery, portal vein and the bile duct, were clamped to produce an ischemic state for 2 hours. Since blood vessels to the remaining parts of the liver were not occluded by this method, portal stasis could be avoided which was of special relevance for circulation stability in rats. Thereafter, occlusion of all vessels was released by removing the clamp to allow reperfusion for 1 hour. The abdominal walls were closed during ischemia and reperfusion.

Using 18 rats in each group, the livers of 6 animals from each group were removed before ischemia, after 2 hours of ischemia, and after 1 hour of reperfusion, respectively. A portion of the liver from each animal was rapidly frozen in liquid nitrogen and used for measurement of glutathione, adenine nucleotides and lipid peroxide. From the remaining portion of the liver, mitochondria was immediately extracted according to the method described by Hogeboom and Schneider in the J. Biol. Chem., Vol. 172, p. 619, 1948. In other experiments, immediately after starting reperfusion, blood from the hepatic vein was collected using 6 rats from each group. These blood samples were then used to measure leaked adenine nucleotides. In addition, after 1 hour of said reperfusion, blood samples were also drawn, which were then used to measure the activity of the leaked liver cell enzymes.

Evaluation of ischemia-reperfusion injury was performed by measuring liver tissue (1) mitochondrial function, (2) glutathione concentration, (3) adenine nucleotides concentration, and (4) lipid peroxide concentration, as well as liver tissue derived (5) adenine nucleotides concentration in the hepatic vein immediately after starting reperfusion, and (6) liver cell enzyme activities in the blood after 1 hour of reperfusion. More specifically, the mitochondrial function in (1) was measured according to the method described by Chance, et al. in Adv. Enzymol., Vol. 17, p. 65, 1956. In addition, the quantitative determination of glutathione in (2) was performed using the same method as Experiment 1 on supernatant obtained by adding 10 vol/g of tissue weight of 2.5% (w/v) sulfosalicylic acid dihydrate aqueous solution to the liver tissue followed by homogenization and centrifugation. In addition, the quantitative determination of adenine nucleotides in (3) was performed by neutralizing the perchloric acid extract of the liver tissue with potassium hydroxide followed by removal of the precipitate and applying to an ion exchange HPLC column according to the method described by Sugino, et al. in J. Chromatogr., Vol. 361, pp. 427–431, 1986. In addition, the measurement of lipid peroxide in (4) was performed according to the thiobarbiturate method described by Ohkawa, et al. in Anal. Biochem., Vol. 95, p. 351, 1979. In addition, the quantitative determination of adenine nucleotides in (5) was performed by centrifuging blood from the hepatic vein to obtain the serum and removing the protein in the serum by centrifugation using a microfilter, followed by applying this to an HPLC column in the same manner as (3). In addition, the measurement of the activities of AST, ALT and LDH, etc. in (6) was performed using Uni-Kit (Chugai Co., Ltd., Tokyo, Japan).

All results were expressed as mean ± standard deviation. Evaluation of significance was performed using Dunnett's test. Cases in which P was less than 0.05 were considered to be statistically significant.

Results

Figure 2A:
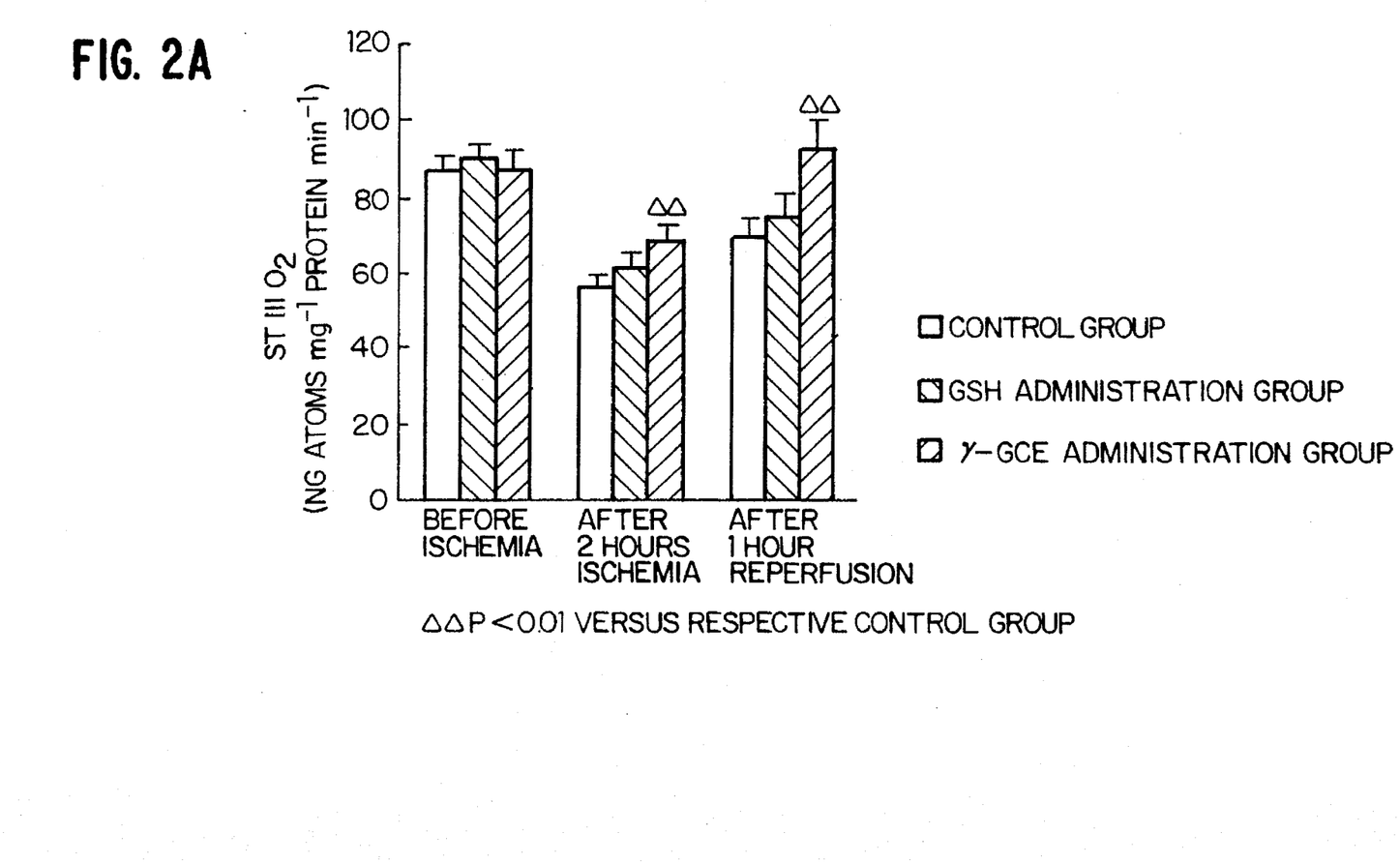
FIG. 2A and FIG. 2B are graphs respectively indicating the preventive and therapeutic effects of γ-GCE on the reduced mitochondrial function during ischemia and the recovery of such during reperfusion in liver ischemia-reperfusion model using rats.
Figure 2B:
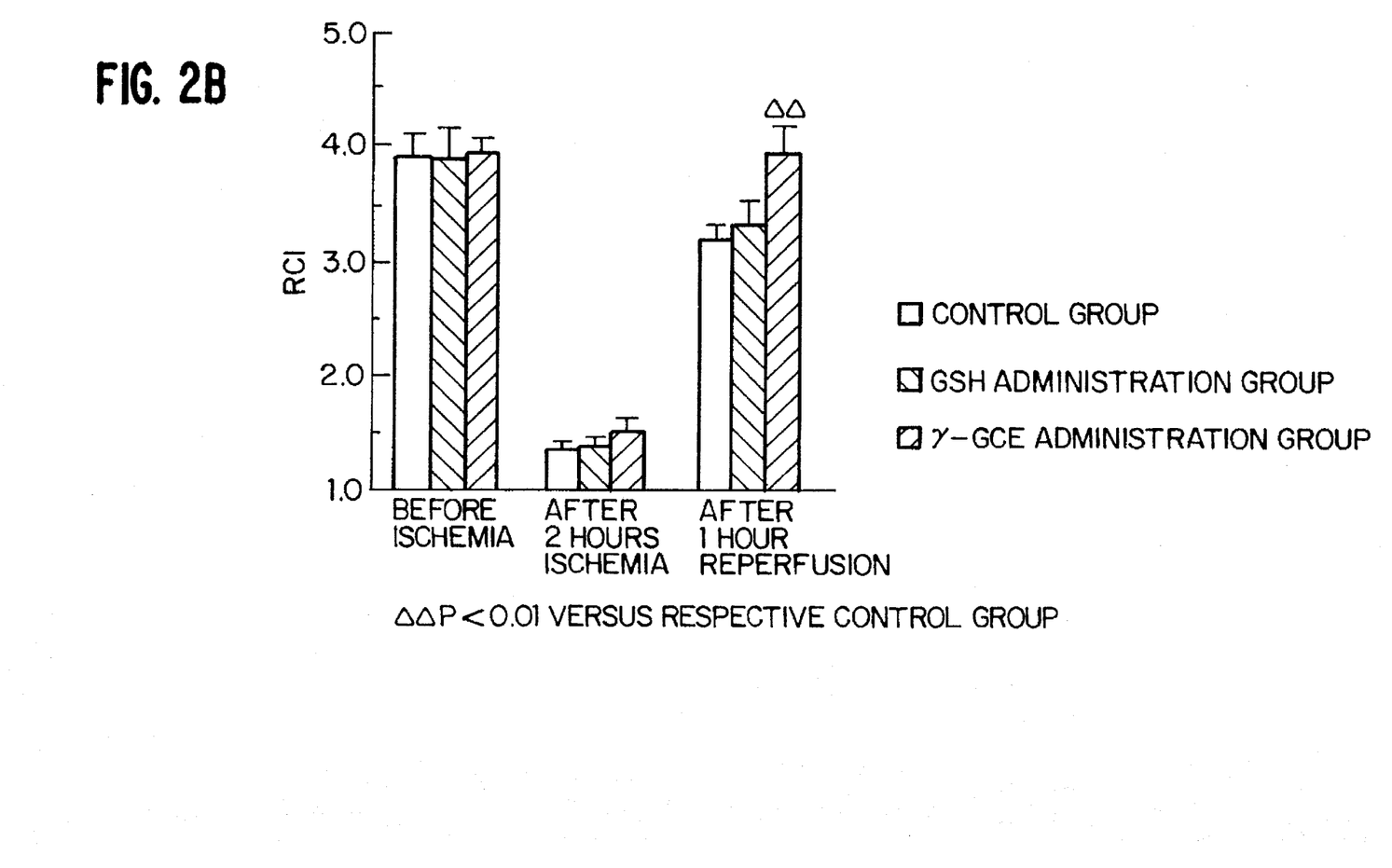

FIG. 2A and FIG. 2B indicate liver tissue mitochondrial function. $\gamma$-GCE significantly suppressed reduction of St. III $O_2$ caused by ischemia, and also significantly promoted recovery of mitochondrial function during reperfusion. In contrast, GSH did not show any protective effects whatsoever.

Table 4 indicates changes in glutathione concentration in liver tissue. In the control and GSH administration groups, glutathione concentration significantly decreased after reperfusion to ca. 60% and 70% of the level prior to ischemia, respectively. In contrast, in the $\gamma$-GCE administration group, no significant decrease was observed throughout the experiment. Moreover, liver glutathione concentration in the $\gamma$-GCE group were significantly higher than in the control group or GSH administration group throughout the experiment.

Table 5 indicates changes in adenine nucleotides concentration in liver tissue. Two hours of ischemia brought about a remarkable decrease in ATP and ADP, while conversely, causing a remarkable increase in AMP. Although $\gamma$-GCE did not show any effects on the reduction of ATP caused by ischemia, it significantly promoted restoration of ATP following reperfusion. GSH did not show any promotive effects on the restoration of ATP.

TABLE 4

Changes in Glutathione Concentrations in Liver Tissue During Liver Ischemia and Reperfusion in Rats

| | Glutathione ($\mu$mol/g of liver wet weight) | | |
|---|---|---|---|
| | GSH | GSSG | GSH + GSSG |
| Before Ischemia | | | |
| Control group | 4.92 ± 0.58 | 0.30 ± 0.05 | 5.22 ± 0.57 |
| GSH group | 4.91 ± 0.35 | 0.38 ± 0.06 | 5.29 ± 0.38 |
| $\gamma$-GCE group | 5.65 ± 0.30* | 0.39 ± 0.07* | 6.04 ± 0.35* |
| After 2 Hours Ischemia | | | |
| Control group | 4.25 ± 0.48 | 0.26 ± 0.04 | 4.51 ± 0.48 |
| GSH group | 4.35 ± 0.65 | 0.35 ± 0.04* | 4.40 ± 0.68 |
| $\gamma$-GCE group | 5.48 ± 0.42** | 0.39 ± 0.01** | 5.87 ± 0.43** |
| After 1 Hour Reperfusion | | | |
| Control group | 3.01 ± 0.53## | 0.20 ± 0.05 | 3.22 ± 0.57## |
| GSH group | 3.40 ± 0.60## | 0.37 ± 0.05** | 3.77 ± 0.64## |
| $\gamma$-GCE group | 4.97 ± 0.25** | 0.54 ± 0.09** | 5.50 ± 0.26** |

All values are expressed as the mean of 6 analytical values ± standard deviation.
*$P < 0.05$; **$P < 0.01$ versus control group
$P < 0.01$ versus before ischemia of the respective group

TABLE 5

Changes in Adenine Nucleotides Concentrations in Liver Tissue During Liver Ischemia and Reperfusion in Rats

| | Adenine Nucleotides ($\mu$mol/g wet liver weight) | | | |
|---|---|---|---|---|
| | ATP | ADP | AMP | ATP + ADP + AMP |
| Before Ischemia | | | | |
| Control group | 2.71 ± 0.15 | 0.85 ± 0.07 | 0.19 ± 0.02 | 3.75 ± 0.18 |
| GSH group | 2.57 ± 0.16 | 0.65 ± 0.06 | 0.18 ± 0.01 | 3.40 ± 0.20* |
| $\gamma$-GCE group | 2.69 ± 0.15 | 0.57 ± 0.05 | 0.13 ± 0.01 | 3.39 ± 0.16* |
| After 2 Hours Ischemia | | | | |
| Control group | 0.05 ± 0.01 | 0.14 ± 0.02 | 0.83 ± 0.08 | 1.02 ± 0.10 |
| GSH group | 0.04 ± 0.01 | 0.13 ± 0.02 | 0.73 ± 0.11 | 0.90 ± 0.11 |
| $\gamma$-GCE group | 0.06 ± 0.01 | 0.17 ± 0.03 | 0.87 ± 0.11 | 1.10 ± 0.10 |
| After 1 Hour Reperfusion | | | | |

TABLE 5-continued

Changes in Adenine Nucleotides Concentrations in Liver
Tissue During Liver Ischemia and Reperfusion in Rats

| | Adenine Nucleotides (μmol/g wet liver weight) | | | |
|---|---|---|---|---|
| | ATP | ADP | AMP | ATP + ADP + AMP |
| Control group | 1.06 ± 0.08 | 0.27 ± 0.02 | 0.09 ± 0.01 | 1.42 ± 0.09 |
| GSH group | 1.13 ± 0.13 | 0.38 ± 0.04** | 0.15 ± 0.02 | 1.66 ± 0.16 |
| γ-GCE group | 1.70 ± 0.02** | 0.38 ± 0.03** | 0.12 ± 0.01 | 2.21 ± 0.03** |

All values are expressed as the mean of 6 analytical values ± standard deviation.
*$P < 0.05$; **$P < 0.01$ versus control group Lipid Peroxide Concentrations Concentration of liver lipid peroxide following reperfusion (9.7±0.7 nmol/mg protein) significantly increased ($P<0.01$) in comparison to concentration after 2 hours of ischemia (6.4±0.6 nmol/mg protein). Administration of γ-GCE significantly suppressed this increase (6.56±0.6 nmol/mg protein, $P<0.01$). However, administration of GSH did not have any protective effects whatsoever (9.1±2.0 nmol/mg protein).

Leakage of Adenine Nucleotides and Liver Cell Enzymes

As indicated in Table 6, γ-GCE significantly reduced the leakage of adenine nucleotides into the hepatic vein observed immediately after starting reperfusion by over 50% and in addition, as indicated in Table 7, γ-GCE significantly reduced leakage of enzymes from liver cells as well observed in the blood following 1 hour of reperfusion. Administration of GSH did not significantly mitigate the leakage of either adenine nucleotides or liver cell enzymes.

TABLE 6

Adenine Nucleotides Concentrations in Hepatic Vein
Immediately After Starting Reperfusion

| | Adenine Nucleotides (μmol/L serum) |
|---|---|
| Control group | 4.23 ± 2.04 |
| GSH group | 3.59 ± 1.28 |
| γ-GCE group | 1.96 ± 0.80* |

All values are expressed as the mean of 6 analytical values ± standard deviation.
$P < 0.05$ versus control group

TABLE 7

Serum AST, ALT and LDH Concentrations
After 1 Hour of Reperfusion

| | IU/L | | |
|---|---|---|---|
| | AZT | ALT | LDH |
| Control group | 4805 ± 1260 | 2957 ± 936 | 39928 ± 14416 |
| GSH group | 3914 ± 1102 | 2337 ± 571 | 26435 ± 12191 |
| γ-GCE group | 2071 ± 625** | 924 ± 330** | 14678 ± 2763** |

All values are expressed as the mean of 6 analytical values ± standard deviation. Abbreviations; AST: Aspartate Amino Transferase, ALT: Alanine Amino Transferase, LDH: Lactate Dehydrogenase.
**$P < 0.01$ versus control group.

The above results indicate that γ-GCE has superior preventive and therapeutic effects against liver ischemia-reperfusion injury.

Example 3

Preventive and therapeutic effects of γ-GCE on the increase in airway responsiveness in an ovalbumin inhalation model using guinea pigs.

Experimental Method

Male Hartley guinea pigs weighing 350–400 g were divided into three groups, i.e., the control group, the ovalbumin (OA) group and the OA+γ-GCE group. The control group was allowed to inhale an aerosol of physiological saline for 7–8 minutes per day for 10 consecutive days. The OA group was allowed to inhale an aerosol of 2% OA in the same manner. The OA+γ-GCE group was allowed to similarly inhale an aerosol of 2% OA together with intraperitoneal administration of 10 mg/kg of γ-GCE twice daily for 10 days.

Evaluation of efficacy was performed by measuring (1) the minimum provocative concentration of acetylcholine (Ach) at which the respiratory resistance reached more than 200% of baseline (Ach Provocative Concentration 200) both before and after inhalation for 10 days, together with measuring (2) the number of pulmonary membrane β-receptors and adenylate cyclase activity, and (3) xanthine oxidase activities in lung tissue, bronchoalveolar lavage fluid and serum, following 10 days of inhalation.

Each of the measurements were made using 6 animals in each group, and the results were expressed as mean ± standard deviation. Evaluation of significance was performed using Dunnett's test. Cases of P being less than 0.05 were considered to be statistically significant.

Results

Figure 3:
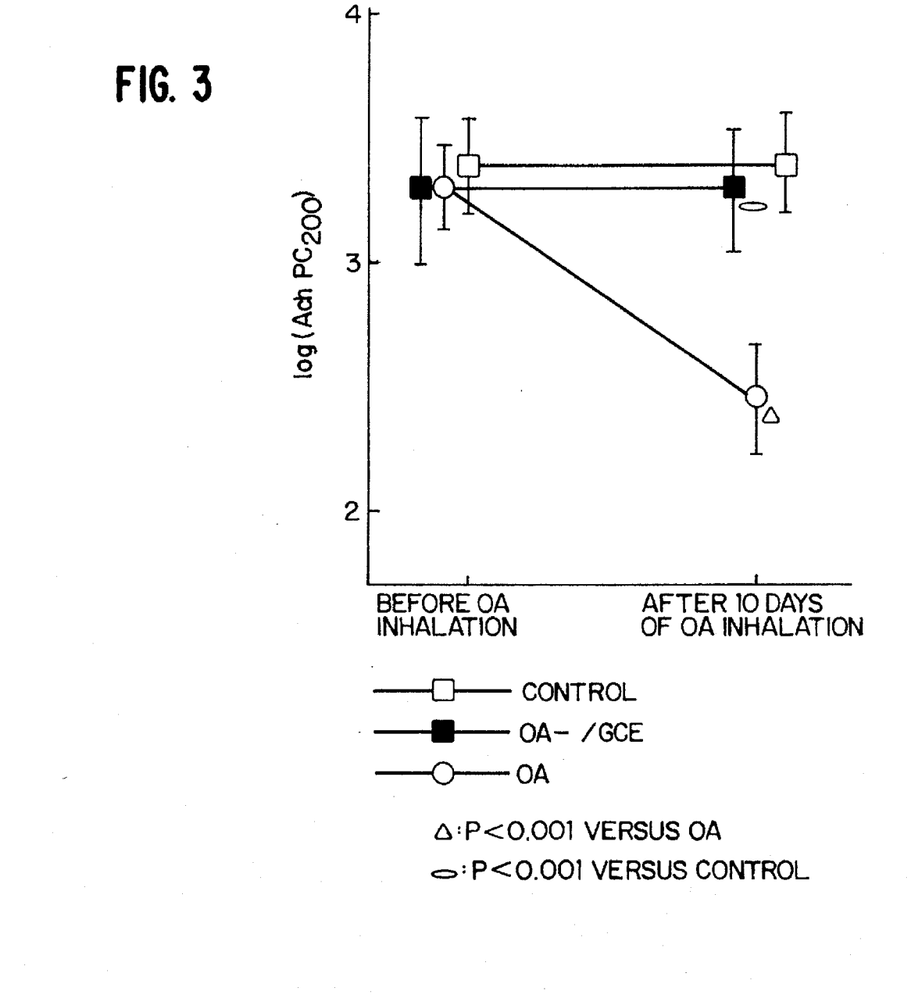
FIG. 3 is a graph indicating the preventive and therapeutic effects of γ-GCE on the increase in airway responsiveness (Ach sensitivity) in ovalbumin inhalation model using guinea pigs.
Figure 4:
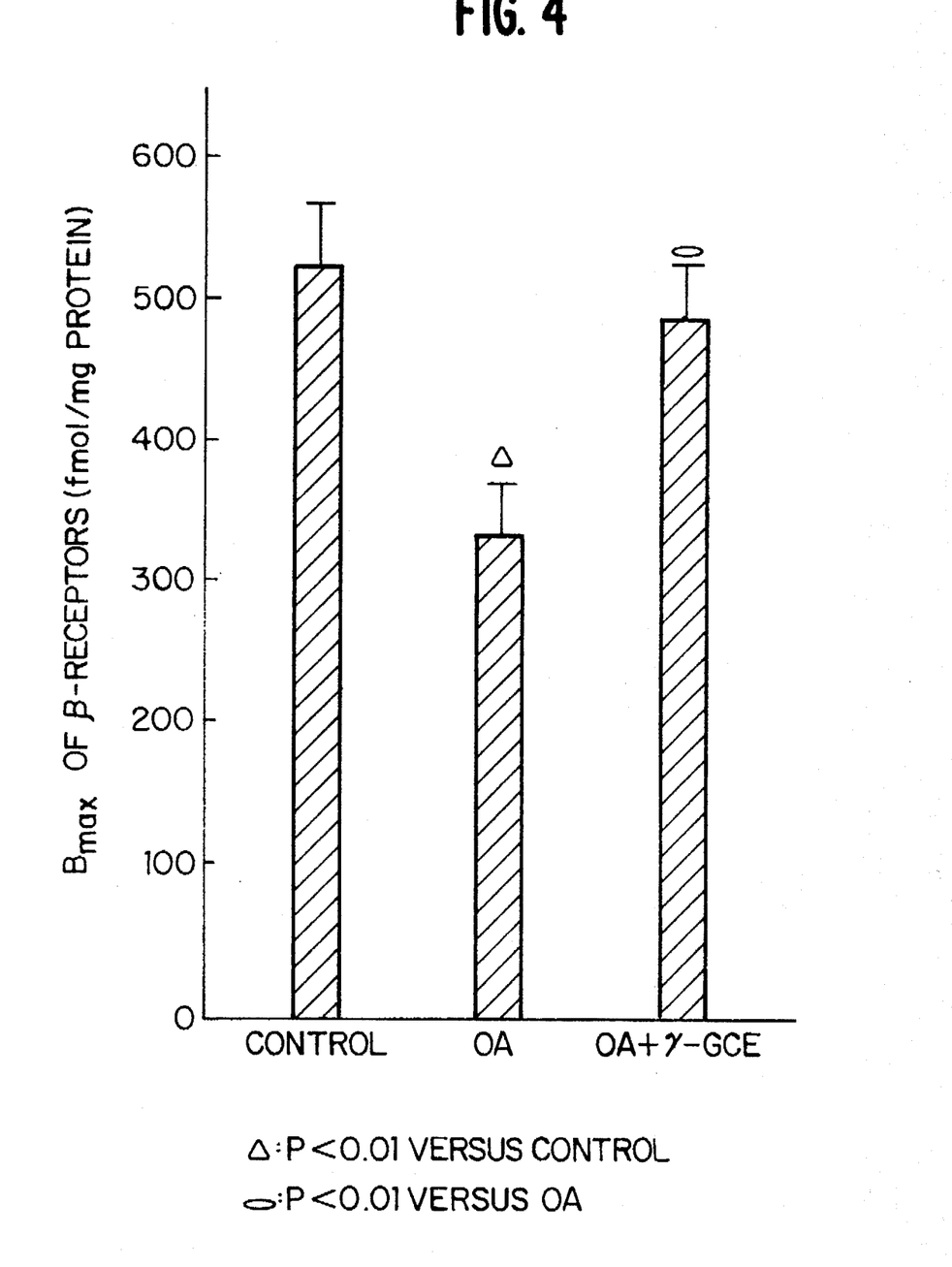
FIG. 4 is a graph indicating the preventive and therapeutic effects of γ-GCE on the reduction in the number of β-receptors on pulmonary membrane in ovalbumin inhalation model using guinea pigs.
Figure 5:
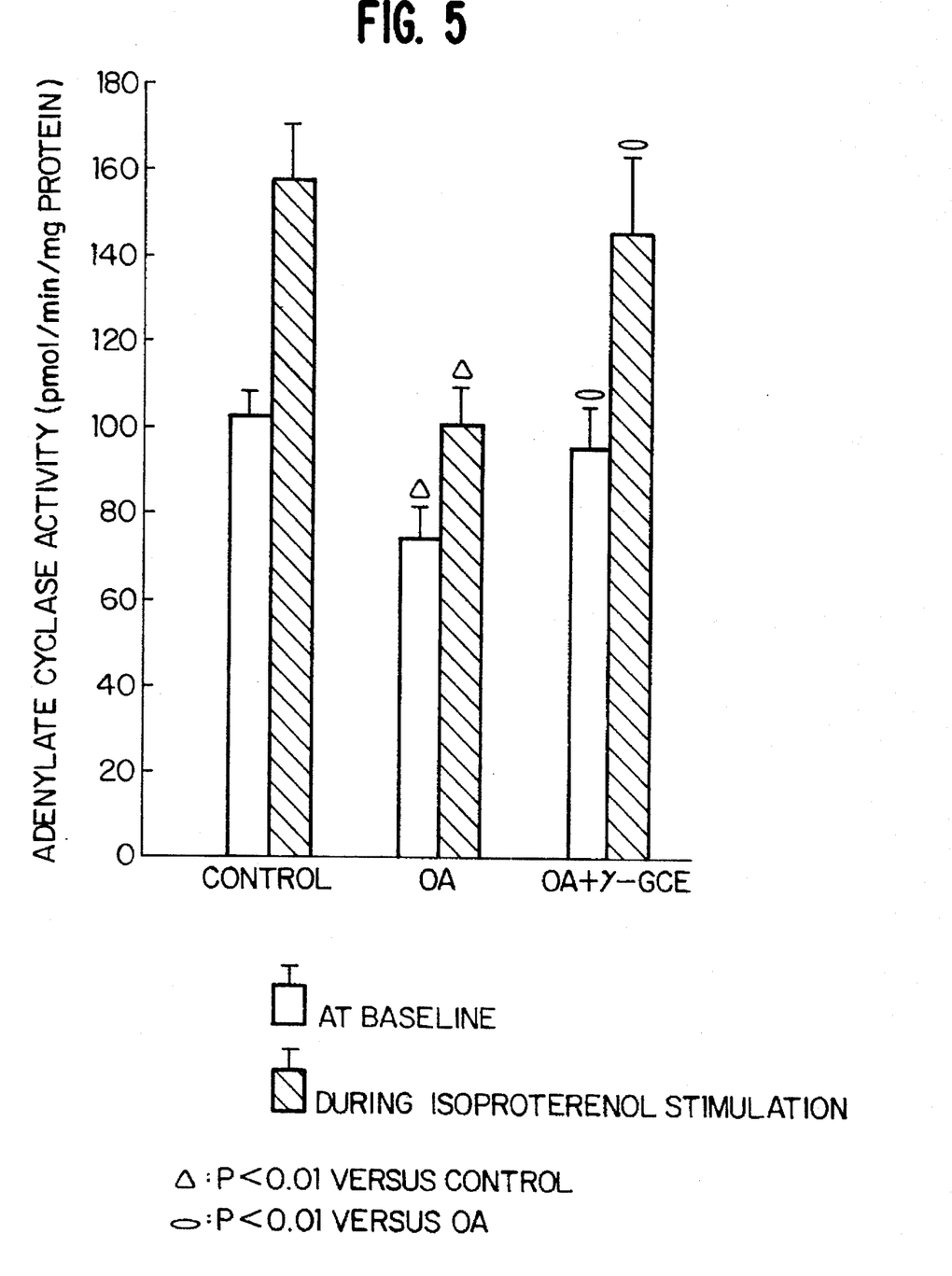
FIG. 5 is a graph indicating the preventive and therapeutic effects of γ-GCE on the decreased adenylate cyclase activity of the pulmonary membrane in ovalbumin inhalation model using guinea pigs.

FIG. 3 indicates the changes in log[Ach $PC_{200}$] as the indicator of airway responsiveness before and after inhalation. FIGS. 4 and 5 indicate the number of pulmonary membrane γ-receptors and pulmonary membrane adenylate cyclase activity after 10 days of inhalation, respectively. Table 8 indicates xanthine oxidase activities in lung tissue, bronchoalveolar lavage fluid and serum following 10 days of inhalation.

TABLE 8

Xanthine Oxidase Activities in Lung Tissue;
Bronchoalveolar Lavage Fluid and Serum

| Test Group | Lung Tissue (mU/g tissue) | Bronchoalveolar Lavage Fluid (mU/ml) | Serum (mU/ml) |
|---|---|---|---|
| Control | 7.35 ± 6.48 | 2.85 ± 1.17 | 3.51 ± 1.15 |
| OA | 49.1 ± 11.7** | 12.6 ± 3.16 | 11.5 ± 2.66* |
| OA + γ-GCE | 33.3 ± 4.02*# | 9.43 ± 0.95*† | 10.0 ± 1.77* |

All values are expressed as mean ± standard deviation.
*$P < 0.01$ versus control group
$P < 0.01$ versus OA group
† $P < 0.05$ versus OA group

Administration of γ-GCE inhibited (1) the remarkable increase in airway responsiveness (remarkable decrease in log[Ach $PC_{200}$]), and (2) the remarkable reduction in membrane β-receptors (38% reduction) as well as the remarkable reduction in membrane adenylate cyclase activity (38% reduction during stimulation by isoproterenol, 28% reduction at baseline), and, despite inhalation of OA, maintained values of such equal to those of no OA inhalation. In addition, xathine oxidase values of the OA+γ-GCE group were also significantly lower than those of the OA group, in lung tissue and bronchoalveolar lavage fluid and so on.

The mechanism of the occurrence of airway hyperresponsiveness (asthma) due to OA inhalation was considered to involve the conversion of xanthine dehydrogenase to xanthine oxidase by some mechanism accompanying OA inhalation, followed by the production of oxygen radicals, which might in turn induce marked acceleration of enzyme conversion and exacerbation of tissue damage including deterioration of receptor function. The above results indicate that γ-GCE has superior preventive and therapeutic effects against various lung diseases including asthma resulted from active oxygens and free radical injury, by inhibiting such vicious circle as a radical scavenger.

We claim:

1. A method for preventing or treating an ischemia-reperfusion tissue injury, comprising administering to a mammal in need thereof an ischemia-reperfusion tissue injury preventing or treating effective amount of: a γ-L-glutamyl-L-cysteine ester compound of formula (I):

wherein R is a straight chain, branched or cyclic hydrocarbon group having 1–10 carbon atoms, or a straight chain or branched hydrocarbon group having 1–5 carbon atoms substituted with an aromatic group; or an oxidized dimer obtained by dehydrogenation between two γ-L-glutamyl-L-cysteine esters having formula (I).

2. The method of claim 1, wherein R is a lower alkyl.

3. The method of claim 2, wherein R is an ethyl group.

4. The method of claim 1, wherein said ischemia-reperfusion tissue injury is an ischemia-reperfusion tissue injury to the heart.

5. The method of claim 1, wherein said ischemia-reperfusion tissue injury is an ischemia-reperfusion tissue injury to the liver.

6. The method of claim 1, wherein said effective amount of said compound or said dimer is between 0.01–5 g/day.

7. The method of claim 6, wherein said effective amount of said compound or said dimer is between 0.01–2.5 g/day.

* * * * *